United States Patent
Huang (10) Patent No.: US 9,841,401 B2
(45) Date of Patent: Dec. 12, 2017

(54) CAPILLARY ELECTROPHORESIS METHOD FOR ANALYZING COLLAGEN

(71) Applicant: NATIONAL CHENG KUNG UNIVERSITY, Tainan (TW)

(72) Inventor: Lynn Ling-Huei Huang, Tainan (TW)

(73) Assignee: National Cheng Kung University, Tainan (TW)

( * ) Notice: Subject to any disclaimer, the term of this patent is extended or adjusted under 35 U.S.C. 154(b) by 656 days.

(21) Appl. No.: 13/723,083

(22) Filed: Dec. 20, 2012

(65) Prior Publication Data

US 2013/0180855 A1 Jul. 18, 2013

Related U.S. Application Data

(63) Continuation-in-part of application No. 12/423,318, filed on Apr. 14, 2009, now abandoned.

(51) Int. Cl.
*G01N 27/447* (2006.01)

(52) U.S. Cl.
CPC . *G01N 27/44704* (2013.01); *G01N 27/44752* (2013.01)

(58) Field of Classification Search
CPC .................... G01N 27/44704; G01N 33/68
See application file for complete search history.

(56) References Cited

U.S. PATENT DOCUMENTS

| | | |
|---|---|---|
| 5,264,101 A | 11/1993 | Demorest et al. |
| 5,462,646 A | 10/1995 | Shieh |
| 2005/0170362 A1* | 8/2005 | Wada et al. ............ 435/6 |

FOREIGN PATENT DOCUMENTS

WO    WO-2008/136321 A1    11/2008

OTHER PUBLICATIONS

Paul Chang, Son Kuan, Gert Eberlein, David Burke, Richard Jones, Characterization of bovine collagens using capillary electrophoresis—an alternative to slab gel electrophoresis, Journal of Pharmaceutical and Biomedical Analysis, vol. 22, Issue 6, Jul. 2000, pp. 957-966, ISSN 0731-7085, http://dx.doi.org/10.1016/S0731-7085(00)00246-6.*

Riis, B.. "Amounts and Variation of Soluble Collagen in Mink Skin During Growth from Kits to Adult Animals", Acta Agriculturae Scandinavica, Section A—Animal Science vol. 50 , Iss. 4,2000.*

L. Huang-Lee et al., "Preparation of Type 1 Collagen Fibrillar Matrices and the Effects of Collagen Concentration of Fibroblast Contraction" Biomed. Eng. Appl. Basis Comm. vol. 5, No. 5, Oct. 1993, pp. 664-675.

(Continued)

*Primary Examiner* — Louis J Rufo
(74) *Attorney, Agent, or Firm* — Muncy, Geissler, Olds & Lowe, P.C.

(57) ABSTRACT

A capillary electrophoresis method for identification and analyzing collagen quantitatively, which is used to identify and quantify collagen in a sample, comprises the steps of: (a) dissolving a collagen-containing sample to form a sample solution; (b) preparing a capillary with an inner wall thereof having a positively-charged layer; (c) introducing the sample solution into the capillary filled with an analytical buffer solution; and (d) driving the sample solution to pass through the capillary. The method of the present invention does not need the purifying pre-treatment and cracking the collagen-containing sample but directly performs the capillary electrophoresis analysis of collagen. Therefore, the present invention can shorten the time for analyzing collagen quantitatively.

18 Claims, 10 Drawing Sheets

(56) References Cited

OTHER PUBLICATIONS

L. Huang et al., "Comparison of epoxides on grafting collagen to polyurethane and their effects on cellular growth", J. Biomed. Mater. Res., 39: Mar. 1998, 630-636.

I. Mikšik et al., "Capillary electromigration methods for the study of collagen", Journal of Chromatography B., 841 (2006) 3-13.

O. Harada et al., "Characterization of Collagen by Capillary Electrophoresis" Bull. Chem. Soc.. Jpn., 69, 3575-3579 (1996).

J. Zhang et al., "Quantitative measurement of collagen methylation by capillary electrophoresis", Electrophoresis 20045, Oct. 25, 2004, 3416-3421.

I. Mikšik et al., "Separation of proteins and peptides by capillary electrophoresis in acid buffers containing high concentrations of surfactants", Journal of Chromatography A, 852 (1999) 325-336.

A. Eckhardt et al., "Separation of low-molecular mass peptides by capillary electrophoresis with the use of alkylamines as dynamic coating agents at low pH", Journal of Chromatography A, 1051 (2004) 111-117.

Huang-Lee at al., "Preparation of Type I Collagen Fibrillar Matrices and the Effects of Collagen Concentration on Fibroblast Concentration," Biomed Eng Appl Nasis Comm, Oct. 1993, pp. 664-675, vol. 5.

Huang et al., "Comparison of Epoxides on Grafting Collagen to Polyurethane and Their Effects on Cellular Growth," J Biomed Mater Res, 1998, pp. 630-636, vol. 39.

B. Zimmerman et al., "Cross-linkages in Collagen," Eur. J. Biochem., vol. 16, pp. 217-225, 1970.

\* cited by examiner

CAPILLARY ELECTROPHORESIS METHOD FOR ANALYZING COLLAGEN

FIELD OF THE INVENTION

The present invention relates to a method for identification and analyzing collagen quantitatively.

BACKGROUND OF THE INVENTION

Collagen extensively and massively exists in the extracellular matrix of connective tissues of animals. A research report (Moseley et al., 2004, Br J Dermatol 150:401-413) points out that collagen may function as a biological marker of disease activity or therapy prognosis. Another research report (Ruszczak, Z., 2003, Adv Drug Deliv Rev 55:1595-1611) points out that collagen scaffold may function as the regenerative environment of cells. Thus, how to accurately detect the quantity of collagen and estimate the rates of reconstruction and degradation of collagen becomes an important subject for the clinical application of collagen.

The conventional methods for quantitatively analyzing collagen include the colorimetric analysis (Stegemann et al., 1967, Clin Chim Acta 18:267-273; Moore, S., 1968, J Biol Chem 243:6281-6283), the high performance liquid chromatography (HPLC), the liquid chromatography tandem mass spectrometry (MS) (Ikeda et al., 1993, J Chromatogr 621:133-138; Kindt et al., 2000, Anal Biochem 283:71-76), and the enzyme linked immunosorbent assay (ELISA) (Bellon, G., 1985, Anal Biochem 150:188-202). However, the abovementioned methods are very complicated and expensive. Therefore, they are not ideal methods for identifying and analyzing collagen quantitatively.

Compared with the abovementioned methods, the capillary electrophoresis is a simpler method for analyzing collagen quantitatively (Deyl, Z & Adam, M, 1989, J Chromatogr 488:161-197; Novotna et al., 1996, J Chromatogr B Biomed Appl 681:77-82; Deyl et al., 1997, J Chromatogr B Biomed Sci Appl 689:181-194; Chalmers, et al., 1999, J Chromatogr Sci 37:443-447). The capillary electrophoresis covers both advantages of electrophoresis and chromatography and can be automated. Therefore, it has been widely used to analyze and identify molecules. In capillary electrophoresis, a voltage is applied to the sample containing different molecules inside a capillary, and different molecules are separated by different electrophoretic mobility and electro-osmotic flow thereof. The silanol groups on the inner wall of the capillary will be dissociated and slightly negatively charged in the solution inside the capillary, particularly in an acidic solution. The negative charges will attract the cations and make the cations distributed on the capillary. When a voltage is applied to the capillary, the cations attached to the inner wall of the capillary will be attracted to the negative pole. The aggregated cations result in viscosity, which will drag the entire solution inside the capillary toward the negative pole and cause a bulk flow of the solution, i.e. the so-called electroosmotic flow. Because of the electrophoretic mobility difference and the electroosmotic flow, the capillary electrophoresis method has a high resolution and a high separation effect. Further, the capillary electrophoresis needs only a small amount of sample because the capillary functions as the electrophoresis path.

In the conventional capillary electrophoresis technology for analyzing collagen quantitatively, the sample should be purified, extracted, and then processed with cyanogen bromide (CNBr) (Deyl, Z & Adam, M, 1989, J Chromatogr 488:161-197; Deyl et al., 1997, J Chromatogr B Biomed Sci Appl 689:181-194; Deyl et al. 1999, J Chromatography A, 852:325-336) or enzymes such as collagenase (Ivan Miks'ik et al. 2006, J Chromatography B, 841:3-13) to obtain polypeptide fragments. The cyanogen bromide enables the cracking reaction of the methionine on the amino acid sequences of protein, and the products of the cracking reaction are analyzed with the capillary electrophoresis method. The collagen cracking reaction is time-consuming and prolongs the process of the collagen analysis. The cyanogen bromide is a toxic material and needs processing and disposing carefully. After purified and extracted, the sample may be processed with enzyme. For example, Harada (Bull. Chem. Soc. Jpn. vol. 69, 1996, pp. 3575-3579) discloses a capillary electrophoresis method for quantitatively identifying the different polypeptides of the collagen. Harada uses commercial pepsin-solubilized collagens (PSCs) as samples, and further digested with pepsin to decrease the telopeptide region. Besides, Harada also discloses a capillary which has a non-charged layer (Brij 35). The Brij is a nonionic surfactant, and it would bind to the polypeptide to form a micelle without carrying any charge. The results of Harada show that a good peak separation for each polypeptide was achieved at pH 5.6-6.5 reflecting various residues of telopeptide. Further, the pretreatments, such as extraction and cracking, should inevitably reduce the total amount of collagen and thus affect the quantitative result of the capillary electrophoresis analysis. Another example is done by Eckhardt (Adam Eckhardt et al., 2004, Journal of Chromatography A, 1051:111-117) and he discloses a capillary electrophoretic system using alkylamines containing background electrolytes at acid pH. To be specific, Eckhardt discloses an analytical buffer with amines, and mix the analytical buffer with different peptides of collagens to form a mixed sample. After that, Eckhardt drives the mixed sample through the capillary and decreases the effects of electro-osmotic flow via the amines with positive charges result in separating the different peptides to measure each amount of peptides. This kind of process "dynamic coating" also can only measure each amount of different peptides with the inevitable reduction and errors on the quantity of total collagen. There are errors while accounting each amount of different peptides, so that when you sum the total amount of each peptide to calculate the total amount of collagen, there is a bigger error. Therefore, it is not accurate enough to measure total amount of collagen via the above methods.

In addition, there are some methods without cracking the native collagen such as the method from Zhang (Jing Zhang et al., 2004, Electrophoresis 25, 3416-3421). Zhang discloses a quantitative measurement of methylated collagen by capillary electrophoresis which proposes an index to quantify the degree of collagen methylation that also correlates with their effects on cell proliferation. Zhang uses a polyvinyl alcohol-coated fused-silica capillary and a phosphate buffer having 0.05% hydroxypropylmthylcellulose to quantify the collagens in which their carboxylic groups were esterified to obtain methylated collagens. In the results of Zhang, the methylated collagens were separated into different peaks using the phosphate buffer with 0.05% hydroxypropylmthylcellulose. Even if Zhang did not crack collagens as the analyte, Zhang can only quantify different methylated collagen respectively with his esterification pretreatment and separation condition rather than quantify the total amount of collagen.

With regard to the novelty, obviousness, and industrial application, an optimal condition for capillary electrophoresis method to identify collagen as a single peak in the chromatogram is required without pretreatment, extraction, purification or further processing the collagen containing sample. Yet, the single peak in the chromatogram can offer an accurate quantification way for total collagen.

SUMMARY OF THE INVENTION

The primary objective of the present invention is to simplify the analysis process of collagen using the capillary electrophoresis method and shorten the analysis time. To achieve the abovementioned objective, the present invention proposes a capillary electrophoresis method for identification and analyzing collagen without cracking into peptides quantitatively in a sample. The method of the present invention comprises steps: dissolving a collagen-containing sample in an acidic solution to form an acidic sample solution; preparing a capillary with the inner wall thereof pre-coated with positively-charged compounds and preferably with an amine group; introducing the acidic sample solution into the capillary containing an analytical solution to elute or separate collagen from other components; and driving the acidic sample solution to pass through the capillary. Preferably, the analytical solution contains phosphate buffer. Preferably, the analytical solution is sodium dihydrogen phosphate buffer solution. The resulting chromatogram has collagen in a single peak no matter types of collagen or with mixed types of collagen.

In comparison to the conventional capillary electrophoresis technology for analyzing collagen quantitatively, the present invention does not need to pre-treat the sample with cyanogen bromide or any enzyme but dissolve the sample directly in an acidic solution, whereby the present invention can greatly reduce the operation time for collagen identification and quantification, and whereby the present invention is exempt from the extraction process and the cracking process, wherefore less collagen is lost in the analysis process, and more accurate result is attained by the capillary electrophoresis method of the present invention.

DETAILED DESCRIPTION OF THE PREFERRED EMBODIMENTS

The present invention provides a capillary electrophoresis method for identification and analyzing collagen quantitatively, wherein a capillary electrophoresis system is used to separate and analyze the sample. The capillary electrophoresis system has an autosampler and at least one kind of wavelength detectors, such as an ultraviolet detector with choice of the detection wavelength. The autosampler includes at least one capillary or micro-channel. The capillary is filled with an analytical buffer solution and equipped with a driving-voltage device at two ends thereof. The operation of the autosampler includes a capillary flushing step, a pneumatic sample injection step, and a sample movement step within the capillary.

The buffer solutions used in the present invention contains an acid solution to effectively dissolve the collagen in the sample and an analytical buffer solution to separate collagen from other components in the capillary, whereby the capillary electrophoresis analysis can have stable results and a single peak indicating collagen can appear in the chromatogram. Both buffer solutions have a pH range between 0.5 to 7.0, preferably between pH 1.0 to 6.0. A better pH for both buffer solutions is about 2~3. The acidic buffer composition comprises at least one acid. The acid component of the buffer can be an inorganic or an organic acid or mixtures thereof. The buffer solution may contain the following components: phosphoric acid solutions, alkali phosphate solutions (such as a sodium dihydrogen phosphate solution), alkali chloride solutions (such as a hydrochloric acid/potassium chloride solution), amino acid solutions (such as a glycine/hydrochloric acid), citric acid solutions (such as a citric acid/sodium citrate), formic acid solutions, acetic acid solutions (such as sodium acetate/acetic acid solution), propionic acid solutions, butyric acid solutions, oxalic acid solutions, tartaric acid solutions, Shikimic acid solutions, and o-phthalic acid solutions (such as a potassium hydrogen phthalate/hydrochloric acid solution). However, the present invention does not limit the buffer solution to have to contain the abovementioned components or only contain the abovementioned solutions.

The capillary used in the present invention may be a capillary having a positively-charged layer pre-coated on the inner wall thereof, particularly an amine capillary having a polymerized amine compound coated on the inner wall thereof. The positively-charged layer can be physically adsorbed or covalently bonded with positively-charged molecules. A great attention of the positively-charged molecules is thru that of amino modification. The amino modifier comprises a vast numbers of compounds, starting from monoamines, such as triethylamine and propylamine, morpholine, N,N-diethylethanolamine, triethanolamine, as well as the quaternary base tetramethylammonium chloride; diamines, such as 1,3 diaminopropane and ethylenediamine;

polyamines, such as chitosan, polylysine, protamines, polyethyleneimine, etc. The amine compound may be a primary amine compound or a material containing ammonium ions. The flushing or pneumatic injection of the capillary will be undertaken in the autosampler of the capillary electrophoresis system.

The collagen sample used in the present invention is sourced from the collagen purified in the laboratory, a commercial available collagen in various forms or as a component of food, cosmetics, medical devices, etc., or the collagen from connective tissues of human beings or animals. The connective tissues may come from skin, intestine, cartilage, tendon, sponge bone, compact bone, and so on. The animal tissue is washed and then cut into pieces. The cut tissue is processed for water content analysis to obtain a dried sample. The dried sample is freeze-ground to obtain a sample, powder. Alternatively, the dried sample is dissolved in an appropriate acidic solution to obtain a sample solution.

To define the range in which the capillary electrophoresis method of the present invention can detect, the samples containing different concentrations of a single type of collagen or multiple types of collagens are respectively injected into the capillaries for analysis. Furthermore, the collagen can be a mixed types of collagen, a denatured collagen, a gelatin, or a mixture of denatured collagen and gelatin, wherein the gelatin has different bloom numbers or molecular weights. The peak areas are obtained by integration and the linear relationship of concentrations is determined to establish the standard curve.

The technical contents of the present invention are described below in details. However, the description is only to demonstrate the present invention but not to limit the scope of the present invention.

In the specification of the present invention, the Beckman P/ACE$^{TE}$ MDQ or PA800 or PA800plus instrument system is used to exemplify the capillary electrophoresis system. The instrument system includes an autosampler, a UV (ultraviolet) detector able to select the detection wavelength, a full-wavelength range PDA (Photodiode Array) detector, and an LIF (Laser Induced Fluorescence) detector. The light source of the UV detector and the full-wavelength range PDA detector is a deuterium lamp emitting light having a wavelength from 190 to 360 nm and the former is equipped with four filters for the wavelengths of 200 nm, 214 nm, 254 nm and 280 nm. The light source of the LIF detector is an argon laser having a wavelength of 488 mm and a diode laser having a wavelength of 635 nm. The autosampler has at least one capillary (or micro-channel) filled with an analytical buffer solution and a driving-voltage device arranged at two ends thereof.

Below are described the embodiments of the present invention and the test results.

Figure 1:
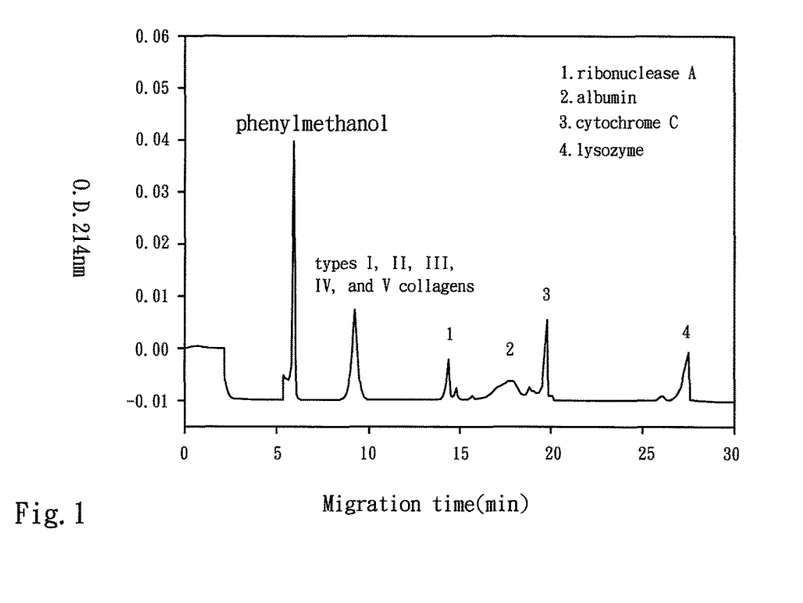
FIG. 1 is a chromatogram obtained from simultaneously detecting various types of collagen and other proteins according to the present invention.

Embodiment I: Collagen Specificity Analysis of the Capillary Electrophoresis Method Prepare a sample of 10 μL of 1 mg/mL collagen solution containing phenylmethanol, wherein the collagen includes type I, II, III, IV, and V. Prepare a sample of a mixed solution of 10 μl of 1 mg/mL albumin and protein mixture (Beckman Cat. No. 477436), wherein the latter contains ribonuclease A, cytochrome C and lysozyme. The abovementioned samples are injected into an amine capillary (a product of Beckman USA and having an inner diameter of 50 μm, an outer diameter of 360 μm and a length of 65 cm) with an injection pressure of 2 psi and an injection time of 6 seconds. The capillary electrophoresis analysis of the abovementioned samples is undertaken in a sodium dihydrogen phosphate solution having a concentration of 50 mM and an acidity of pH2.5, at a temperature of 25° C., under an electrophoresis voltage of −25 KV, and with an UV absorption wavelength of 214 nm. The analysis result is shown in FIG. 1. The peaks of phenylmethanol, collagen, ribonuclease A, albumin, cytochrome C and lysozyme sequentially appear in the migration time axis, which means that the capillary electrophoresis method of the present invention has a pretty high specificity in identifying collagen and can effectively measure the total amount of collagen.

Embodiment II: The Sensitivity of the Capillary Electrophoresis Method and the Standard Curve Analysis To define the range the capillary electrophoresis method of the present invention can detect and to establish the standard curve for collagen analysis, different amounts of type I collagen are injected into an amine capillary (a product of Beckman USA and having an inner diameter of 50 μm, an outer diameter of 360 μm and a length of 65 cm) with an injection pressure of 2 psi and an injection time of 6 seconds. The type I collagen samples have amounts of 276.8, 207.6, 138.4, 83.6, 76.14, 69.21, 55.37, 54.58, 47.46, 41.53, 35.59, 33.22, 27.76, 23.73, 17.79, 13.76, 11.86, 6.29, 4.88, 3.46, 2.76, 1.73, 1.37, 1.09, 0.9, 0.46, 0.27, 0.16, 0.13, 0.09, 0.06, 0.05 ng respectively. The capillary electrophoresis analyses are undertaken in a sodium dihydrogen phosphate buffer solution having a concentration of 50 mM and an acidity of pH2.5, at a temperature of 25° C., under an electrophoresis voltage of −25 KV, and with an UV absorption wavelength of 214 nm. The peak areas are obtained by integration and the linear relationship of concentrations is determined to establish the standard curve.

Figure 2A:
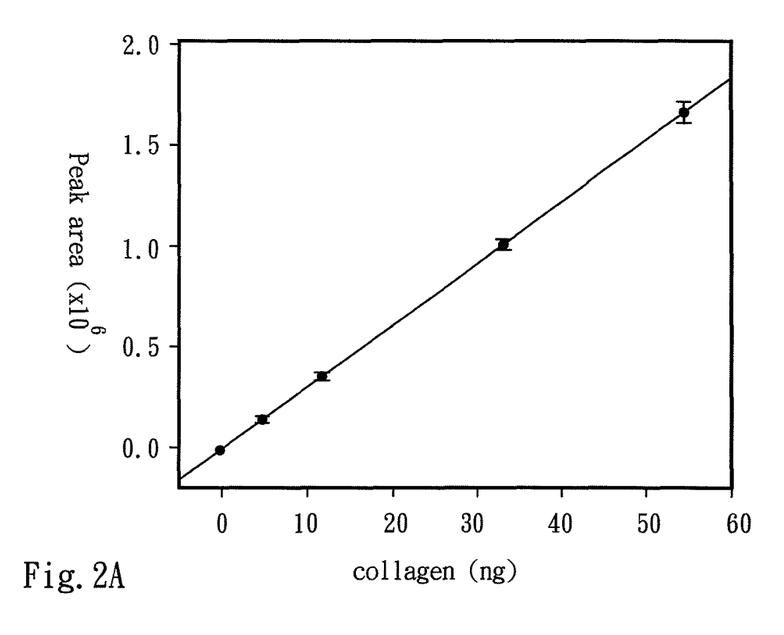
FIG. 2A is a diagram showing the linear regression of the peak areas obtained from detecting collagen with concentrations between 0 and 60 ng according to the present invention.
Figure 2B:
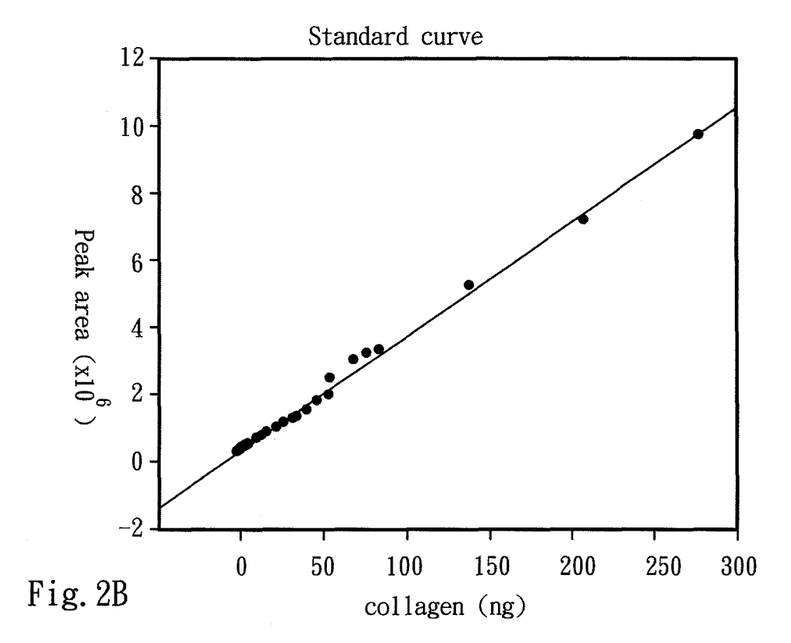
FIG. 2B is a diagram showing the linear regression of the peak areas obtained from detecting collagen with concentrations between 0 and 300 ng according to the present invention.

The results of the abovementioned tests are shown in FIG. 2A and FIG. 2B. The maximum and minimum amounts of collagen detected by the capillary electrophoresis method of the present invention are 276.8 ng and 0.05 ng respectively. Therefore, the capillary electrophoresis method of the present invention has a larger detection range than the conventional technology. Furthermore, a linear relationship is obtained between the peak area and the collagen content. When the sample containing 0.05 ng of collagen is tested for 20 times successively, the average value of peak areas, the standard deviation, and the relative standard deviation of the peak areas are 14379, 940 and 6.5% respectively. Therefore, the capillary electrophoresis method of the present invention has high reproducibility and reliability. As the relative standard deviation in detecting 0.05 ng of collagen is lower than 15%, 0.05 ng may be used as the detection sensitivity of the capillary electrophoresis method of the present invention.

Embodiment III: Quantitative Analysis of Collagen in Connective Tissue

The connective tissues used in the tests may come from skin, intestines, cartilage, tendon, sponge bone or compact bone of pigs. All the connective tissues are divided into four groups of samples. The four groups of samples are analyzed respectively with (a) a hydroxypro line colorimetric reaction method, (b) a first capillary electrophoresis method for hydroxyproline detection, (c) a second capillary electrophoresis method for hydroxyproline detection, and (d) the capillary electrophoresis method of the present invention for collagen analysis.

Firstly, the redundant fat and muscle is removed from the connective tissues of pigs. Next, the connective tissues are flushed with pure water and a phosphate solution to remove blood and dirt. The connective tissues are then cut into tiny pieces (about 1 mm$^3$). Next, the cut tissues are weighed to get the wet weights thereof and then lyophilized for about 24 hours or more to get constant dry weights, whereby the water content of tissue samples is learned, and dried tissue samples are obtained. Next, the dried tissue samples are freeze-ground into powders with a cryogenic grinder (a product of SPEX CertiPrep, Inc.). The powders are then dissolved in a 0.5M acetic solution and the mixture is agitated with a homogenizer (a product of Polytron®, Kinematica AG, Switzerland) and a sonicator (a product of Quantrex 280H, Ultrasonices, L&R Manufacturing, Co., USA) to attain homogeneous collagen solutions with appropriate concentration. Then, the collagen solutions are stored at a temperature of 4° C. for analysis.

(A) Hydroxyproline Colorimetric Reaction Method

The connective tissues of pigs are freeze-ground into powders. The powders are decomposed in a 6N hydrochloric acid solution by a ratio of 0.5 mg sample and 0.5 ml hydrochloric acid solution at 110° C. for 24 hours. The product is then mixed with chloramines T and the Ehrlich's reagent for a colorimetric reaction (according to Huang-Lee, L L H & Nimni, M E, 1993, Biomed Eng Appl Basis Comm 5: 664-675). The products of the colorimetric reaction are analyzed with an enzyme-linked immunosorbent assay device (the ELISA reader and the VERSAmax microplate reader, Molecular Devices, USA). The content of hydroxyproline is calculated from the absorbance at a wavelength of 550 nm in comparison to a standard curve. The total amount of collagen is estimated according to the ratio that hydroxyproline conventionally exists in collagen. The calculation formula is collagen concentration=hydroxyproline concentration×7.46.

(B) A First Capillary Electrophoresis Method for Hydroxyproline Detection

The connective tissues of pigs are freeze-ground into powders. The powders are decomposed in a 6N hydrochloric acid solution by a ratio of 0.5 mg sample and 0.5 ml hydrochloric acid solution at 110° C. for 24 hours. The decomposed product is vacuum-dried in the presence of sodium chloride to remove hydrochloric acid. The dried product is re-dissolved in a 0.5M sodium hydrogen carbonate buffer solution by a ratio of 0.5 mg dried product: 0.5 ml buffer solution. The re-dissolution liquid is mixed with a fresh 0.02M dansyl chloride/acetone solution by a volume ratio of 1:1, and the mixture solution is placed in a 65° C. dry bath incubator for 40 minutes to enable a derivative reaction. After the derivative reaction, the sample solution is injected into an uncoated capillary (a product of Beckman USA and having an inner diameter of 50 μm and a length of 60.2 cm) with an injection pressure of 0.5 psi and an injection time of 20 seconds. The capillary electrophoresis analysis is undertaken in a borate/phosphate buffer solution, at a temperature of 25° C., under an electrophoresis voltage of 27 kV, and, with an UV absorption wavelength of 214 nm, wherein the ratio of (0.02M borate/phosphate, 0.1M SDS, pH9): methanol=9:1. The result of the capillary electrophoresis analysis is compared with a hydroxyproline calibration curve to obtain the hydroxyproline content in the sample. The total amount of collagen is estimated according to the ratio that hydroxyproline conventionally exists in collagen.

(C) A Second Capillary Electrophoresis Method for Hydroxyproline Detection

The connective tissues of pigs are freeze-ground into powders. The powders are decomposed in a 6N hydrochloric acid solution by a ratio of 0.5 mg sample and 0.5 ml hydrochloric acid solution at 110° C. for 24 hours. After the decomposition reaction, sodium hydroxide is added to neutralize the hydrochloric sample solution. The neutralized sample solution is mixed with a 0.5M sodium hydrogen carbonate buffer solution by a volume ratio of 1:1. The buffered sample solution is mixed with a fresh dansyl chloride/acetone solution by a volume ratio of 1:1, and the mixture solution is placed in a 65° C. dry bath incubator for 40 minutes to enable a derivative reaction. After the derivative reaction, the sample solution is injected into an uncoated capillary (a product of Beckman USA and having an inner diameter of 50 μm and a length of 60.2 cm) with an injection pressure of 0.5 psi and an injection time of 20 seconds. The capillary electrophoresis analysis is undertaken in a borate/phosphate buffer solution, at a temperature of 25° C., under an electrophoresis voltage of 27 kV, and, with an UV absorption wavelength of 214 nm, wherein the ratio of (0.02M borate/phosphate, 0.1M SDS, pH9): methanol=9:1. The result of the capillary electrophoresis analysis is compared with a hydroxyproline calibration curve to obtain the hydroxyproline content in the sample. The total amount of collagen is estimated according to the ratio that hydroxyproline conventionally exists in collagen.

(D) Capillary Electrophoresis Method of the Present Invention for Collagen Analysis The connective tissues of pigs are freeze-ground into powders. The powder is dissolved in a 0.5M acetic solution, and the mixture of the powder and the acetic solution is homogenized. The homogenized tissue solution is injected into an amine capillary (a product of Beckman USA and having an inner diameter of 50 μm, an outer diameter of 360 μm and a length of 65 cm) with an injection pressure of 2 psi and an injection time of 6 seconds. The capillary electrophoresis analysis is undertaken in a sodium dihydrogen phosphate buffer solution having a concentration of 50 mM and an acidity of pH2.5, at a temperature of 25° C., under an electrophoresis voltage of −25 KV, and with an UV absorption wavelength of 214 nm, whereby collagen can be directly identified. The content of collagen is worked out from the area of the peak.

The test results of the abovementioned four quantitative analysis methods for collagen in connective tissues are shown in Table 1.

TABLE 1

| | Water content (%) | Method (A) (%) | Method (B) (%) | Method (C) (%) | Method (D) (%) |
|---|---|---|---|---|---|
| Pig Skin | 61.9 ± 0.6 | 23.7 ± 2.7 | 20.7 ± 2.8 | 22.3 ± 1.5 | 23.8 ± 2.9 |
| Pig Intestine | 84.9 ± 0.8 | 1.1 ± 0.3 | 1.1 ± 0.3 | 1.0 ± 0.2 | 0.8 ± 0.2 |
| Pig Cartilage | 70.1 ± 0.7 | 14.6 ± 1.2 | 12.5 ± 0.7 | 14.5 ± 0.7 | 10.1 ± 2.9 |
| Pig Tendon | 61.2 ± 0.6 | 32.9 ± 2.6 | 29.0 ± 4.3 | 28.7 ± 0.4 | 30.5 ± 2.7 |
| Spongy Bone | 34.5 ± 2.2 | 4.1 ± 1.5 | 4.1 ± 1.1 | 4.1 ± 0.7 | 4.1 ± 0.8 |
| Compact Bone | 21.6 ± 1.4 | 15.2 ± 0.9 | 12.9 ± 3.1 | 11.8 ± 0.6 | 15.1 ± 4.0 |

From the quantitative analysis results of collagen in connective tissues taken from the same source, the collagen contents detected by different analysis methods have negligible variation. Compared with the conventional technology that indirectly obtains the collagen content via analyzing the hydroxyproline content, the capillary electrophoresis method of the present invention can detect the collagen and measure the collagen content directly.

Embodiment IV: Quantitative Analysis of Collagen which Contaminated with Some Anion or Polyanion Compounds In case of collagen samples contaminated with some anion or polyanion compounds such as hyaluronan (HA), the samples will be further treated with excess of cation or polycation compounds such as chitosan, polyamines, hexadecyltrimethylammonium bromide (CTAB), poly-allylamine hydrochloride, etc. to remove the anion or polyanion contaminants.

(A) Quantitative Analysis of Collagen with CTAB

Prepare a 1.0 ml 10% CTAB solution by dissolving 0.1 g hexadecyltrimethylammonium bromide (HTAB, Riedel-de-Haen, Cat. No. 65015) into double distilled water and heat at 50° C. for 10 minutes until the CTAB solution is limpid. Prepare the samples of collagen with CTAB and the samples of collagen-HA (HA is 12 kD, 780 kD or 1500 kD) with CTAB by the ratio of table 2 and place at room temperature for 1 hour.

TABLE 2

| Collagen (5 mg/ml)vol. (μl) | 10% CTAB vol. (μl) | 0.5M CH₃COOH vol.(μl) |
|---|---|---|
| 10 | 0 | 10 |
| 10 | 1 | 9 |
| 10 | 2 | 8 |
| 10 | 4 | 6 |

| Collagen-HA (5 mg/ml-2 mg/ml) vol. (μl) | 10% CTAB vol. (μl) | 0.5M CH₃COOH vol. (μl) |
|---|---|---|
| 10 | 0 | 10 |
| 10 | 1 | 9 |
| 10 | 2 | 8 |
| 10 | 4 | 6 |

Figure 3:
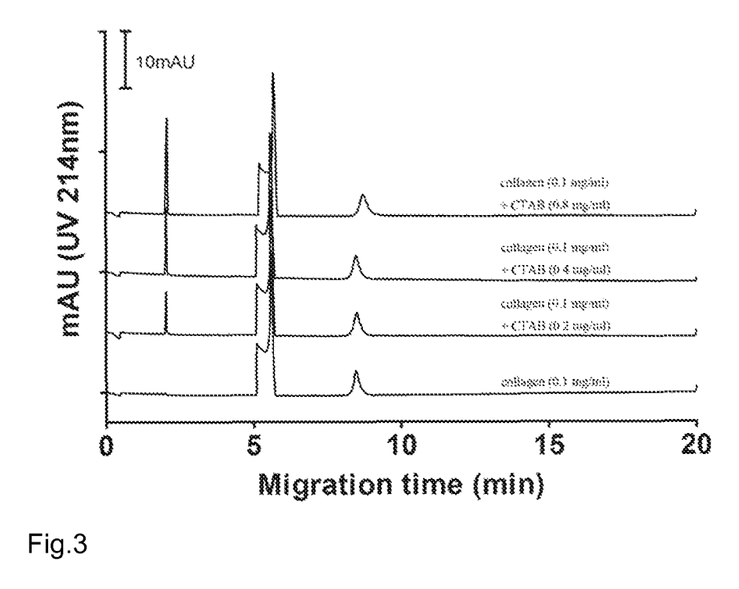
FIG. 3 is an electrophoresis chromatogram obtained in detecting collagen along and collagen with different concentrations of CTAB according to the present invention.
Figure 4:
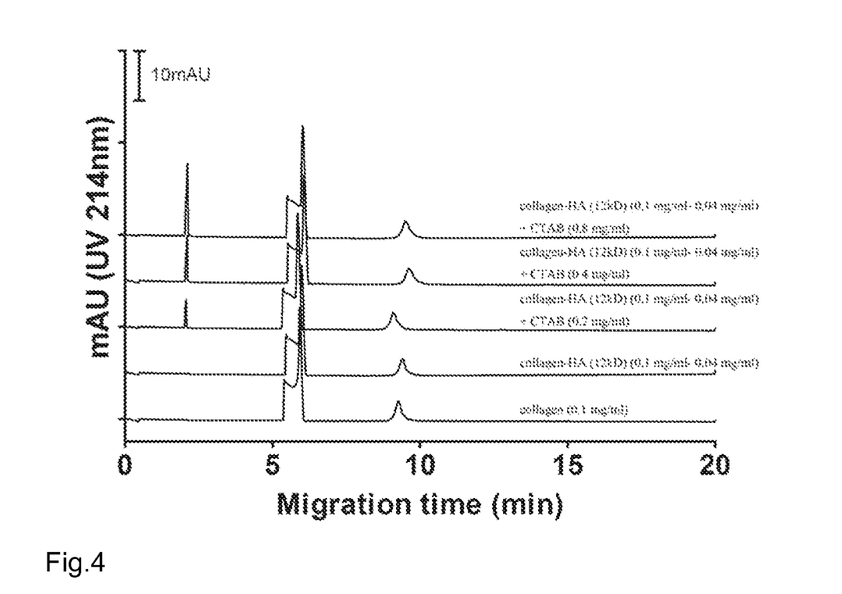
FIG. 4 is an electrophoresis chromatogram obtained in detecting collagen with 12 kD HA and collagen with 12 kD HA and different concentrations of CTAB according to the present invention.
Figure 5:
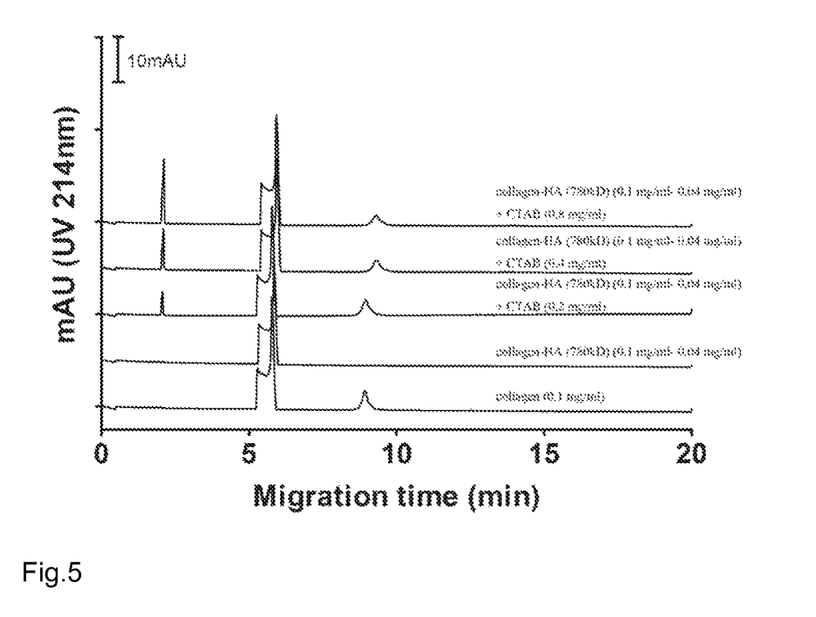
FIG. 5 is an electrophoresis chromatogram obtained in detecting collagen with 780 kD HA and collagen with 780 kD HA and different concentrations of CTAB according to the present invention.
Figure 6:
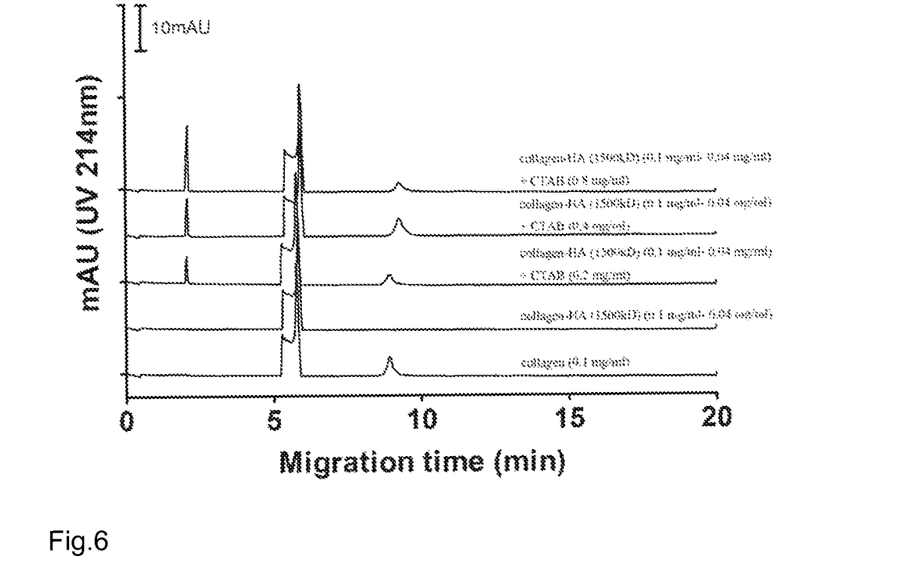
FIG. 6 is an electrophoresis chromatogram obtained in detecting collagen with 1500 kD HA and collagen with 1500 kD HA and different concentrations of CTAB according to the present invention.

Centrifuge the samples for 5 minutes and mix 8 μl supernatant with 1.92 μl 0.5M CH$_3$COOH to prepare the determinants. Take 200 μl of each determinant to mix with 100× 0.5 μl diluted neutral marker and then analyzed by the capillary electrophoresis. The results are shown in FIGS. 3 to 6. In FIG. 3, when the ratio of CTAB raising to 20% the peak of collagen without HA, the peak is more widely than the peak with collagen only. The results shown in FIGS. 4 and 6 find out that CTAB can decrease the influence from HA. In FIG. 4 the preferring ratio of CTAB is 5-20% when the HA is 12 kD. In FIG. 5 the preferring ratio of CTAB is 5% when the HA is 780 kD. In FIG. 6 the preferring ratio of CTAB is 10% when the HA is 1500 kD.

(B) Quantitative Analysis of Collagen with Chitosan

Prepare a 1% chitosan solution by dissolving 5 mg chitosan (Wako, Cat. No. 031-14301, FW=2000-5000) into 0.5 ml double distilled water and diluted to 0.5% chitosan solution with double distilled water. Prepare the samples of collagen with chitosan solution and the samples of collagen-HA (12 kD and 780 kD) with chitosan solution by the ratio of table 3 and place at 4° C. for 16~18 hours.

TABLE 3

| Collagen (5 mg/ml)vol. (μl) | 0.5% Chitosan solution vol. (μl) | 0.5M CH₃COOH vol.(μl) |
|---|---|---|
| 10 | 0 | 10 |
| 10 | 1 | 9 |
| 10 | 2 | 8 |
| 10 | 4 | 6 |

| Collagen-HA(5 mg/ml-2 mg/ml) vol. (μl) | 0.5% Chitosan solution vol. (μl) | 0.5M CH₃COOH vol. (μl) |
|---|---|---|
| 10 | 0 | 10 |
| 10 | 1 | 9 |
| 10 | 2 | 8 |
| 10 | 4 | 6 |

Figure 7:
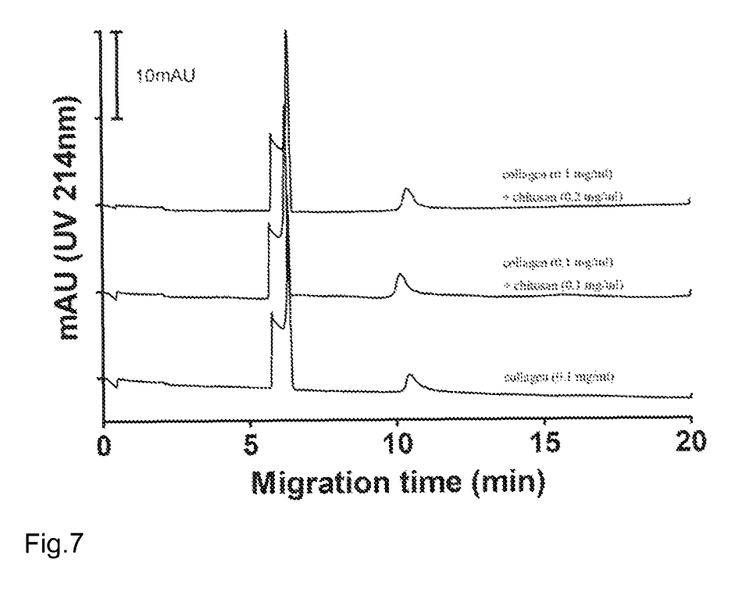
FIG. 7 is an electrophoresis chromatogram obtained in detecting collagen along and collagen with different concentrations of chitosan according to the present invention.
Figure 8:
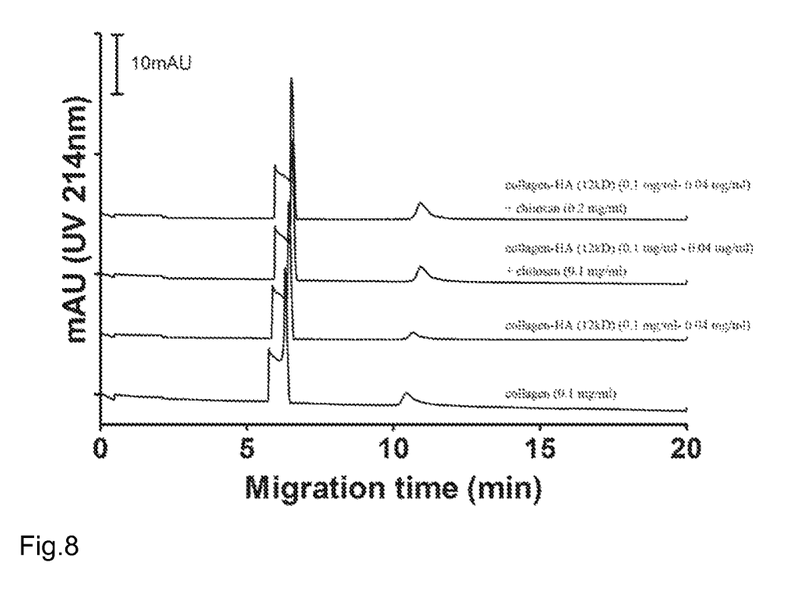
FIG. 8 is an electrophoresis chromatogram obtained in detecting collagen with 12 kD HA and collagen with 12 kD HA and different concentrations of chitosan according to the present invention.
Figure 9:
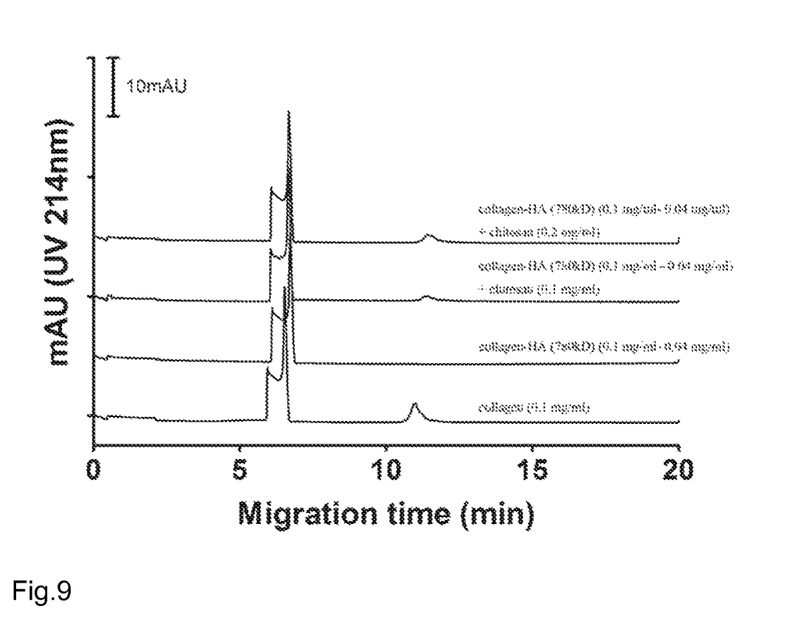
FIG. 9 is an electrophoresis chromatogram obtained in detecting collagen with 780 kD HA and collagen with 780 kD HA and different concentrations of chitosan according to the present invention.

Centrifuge the samples for 5 minutes and mix 8 μl supernatant with 192 μl 0.5M CH$_3$COOH to prepare the determinants. Take 200 μl of each determinants to mix with 100× 0.5 μl diluted neutral marker and then analyzed by the capillary electrophoresis. The results are shown in FIGS. 7 to 9. In FIG. 7, chitosan seems to increase the signal of collagen without HA. The results shown in FIGS. 4 and 6 find out that chitosan can also decrease the influence from HA. In FIG. 8 the preferring ratio of chitosan to collagen with HA is 1:1 or 2:1 when the HA is 12 kD. In FIG. 9 the preferring ratio of chitosan to collagen with HA is 1:1 when the HA is 780 kD.

As the capillary electrophoresis method for analyzing collagen of the present invention is exempt from the pretreatment of purification, extraction, and processing with cyanogen bromide used in the conventional technology, the present invention can greatly shorten the time for analysis. From the embodiments described above, it is known that the capillary electrophoresis method of the present invention can detect a large range of collagen concentration and quantify the total amount of collagen in tissue. Furthermore, the method of the present invention has high specificity for collagen identification and sensitivity when the collagen is mixed with other types of proteins. Therefore, the present invention has improvements over the conventional technology and possesses novelty and non-obviousness—the conditions for a patent. Comparing with the dynamic coating method, the pre-coated capillary of the present invention can apply to directly measure the total amount of collagen of the sample accurately and decrease the errors of calculating. The current invention provides a special condition for using capillary electrophoresis method to identify collagen as a single peak in the chromatogram disregarding its typing and thus the total amount of collagen can be accurately quantitated. Thus, the inventor files the application for a patent. It will be appreciated if the patent is approved fast.

The present invention has been described in detail with the embodiments. However, the embodiments are only to exemplify the present invention but not to limit the scope of the present invention. Any equivalent modification or variation according to the spirit of the present invention is to be also included within the scope of the present invention.

What is claimed is:
1. A capillary electrophoresis method for analyzing collagen without cracking the collagen into polypeptides, which is used to identify collagen and quantify the total amount of collagen in a sample, comprising the steps of:
dissolving a collagen-containing sample to form a sample solution, wherein the collagen containing sample contains the collagen that is not cracked into polypeptides;

preparing a capillary with an inner wall thereof already pre-coated a positively-charged layer;

introducing said sample solution into said capillary having an analytical buffer solution, wherein said analytical buffer solution has a pH between 0.5~7.0;

driving said sample solution to pass through said capillary under a negative electrophoresis voltage; and having collagen peak in a single peak in a resulted chromatogram for any type of single or mixed collagen within a 10 minute period, and measuring the total amount of collagen in the sample according to the area of the peak in the resulted chromatogram, thus the collagen can be identified and accurately quantitated.

2. The capillary electrophoresis method for identification and analyzing collagen quantitatively according to claim 1, wherein said analytical buffer solution has a pH between 2~3.

3. The capillary electrophoresis method for identification and analyzing collagen quantitatively according to claim 1, wherein said analytical buffer solution is selected from a group consisting of an inorganic acid, an organic acid and mixtures of inorganic acid and organic acid.

4. The capillary electrophoresis method for identification and analyzing collagen quantitatively according to claim 1, wherein said analytical buffer solution is selected from a group consisting of phosphoric acid solutions, alkali phosphate solutions, alkali chloride solutions, amino acid solutions, citric acid solutions, formic acid solutions, acetic acid solutions, propionic acid solutions, butyric acid solutions, oxalic acid solutions, tartaric acid solutions, Shikimic acid solutions, and o-phthalic acid solutions.

5. The capillary electrophoresis method for identification and analyzing collagen quantitatively according to claim 1, wherein said analytical buffer solution is phosphate solution.

6. The capillary electrophoresis method for identification and analyzing collagen quantitatively according to claim 1, wherein said collagen-containing sample is dissolved in an acidic solution.

7. The capillary electrophoresis method for identification and analyzing collagen quantitatively according to claim 6, wherein said acidic solution is an acetic acid solution.

8. The capillary electrophoresis method for identification and analyzing collagen quantitatively according to claim 1, wherein said inner positively-charged layer is an amine compound.

9. The capillary electrophoresis method for identification and analyzing collagen quantitatively according to claim 8, wherein said amine compound contains ammonium ions.

10. The capillary electrophoresis method for identification and analyzing collagen quantitatively according to claim 8, wherein said amine compound is a primary amine compound.

11. The capillary electrophoresis method for identification and analyzing collagen quantitatively according to claim 1, wherein said collagen is a mixed types of collagen.

12. The capillary electrophoresis method for identification and analyzing collagen quantitatively according to claim 1, wherein said collagen is selected from any type of collagen.

13. The capillary electrophoresis method for identification and analyzing collagen quantitatively according to claim 1, wherein said collagen is selected from a group consisting of a denatured collagen, a gelatin, and a mixture of denatured collagen and gelatin.

14. The capillary electrophoresis method for identification and analyzing collagen quantitatively according to claim 13, wherein said gelatin has different bloom numbers or molecular weights.

15. The capillary electrophoresis method for identification and analyzing collagen quantitatively according to claim 1 further comprising a detection means for detecting collagen passing through said capillary.

16. The capillary electrophoresis method for identification and analyzing collagen quantitatively according to claim 15, wherein said detection means detects a wavelength of 214 nm with an ultraviolet absorption spectrum method.

17. The capillary electrophoresis method for identification and analyzing collagen quantitatively according to claim 1, wherein the sample solution comprises chitosan.

18. The capillary electrophoresis method for identification and analyzing collagen quantitatively according to claim 1, wherein the sample solution comprises hexadecyltrimethylammonium bromide.

* * * * *